(12) United States Patent
Sandberg et al.

(10) Patent No.: US 9,120,873 B2
(45) Date of Patent: Sep. 1, 2015

(54) RECOMBINANTLY PRODUCED HUMAN FACTOR VIII AND IX

(75) Inventors: Helena Sandberg, Bromma (SE); Peter Stenlund, Bromma (SE); Carola Schröder, Neuried (DE); Elisabeth Casademunt, München (DE); Maya Tiemeyer, München (DE)

(73) Assignee: Octapharma AG, Lachen (CH)

( * ) Notice: Subject to any disclaimer, the term of this patent is extended or adjusted under 35 U.S.C. 154(b) by 412 days.

(21) Appl. No.: 12/737,815

(22) PCT Filed: Aug. 21, 2009

(86) PCT No.: PCT/EP2009/060829
§ 371 (c)(1),
(2), (4) Date: Jul. 5, 2011

(87) PCT Pub. No.: WO2010/020690
PCT Pub. Date: Feb. 25, 2010

(65) Prior Publication Data
US 2011/0262424 A1    Oct. 27, 2011

Related U.S. Application Data

(60) Provisional application No. 61/136,250, filed on Aug. 21, 2008.

(30) Foreign Application Priority Data

Aug. 21, 2008  (EP) .................................... 08162765

(51) Int. Cl.
| | | |
|---|---|---|
| A61K 38/14 | (2006.01) | |
| A61K 38/37 | (2006.01) | |
| C07K 2/00 | (2006.01) | |
| C07H 21/04 | (2006.01) | |
| C12P 21/04 | (2006.01) | |
| C12P 21/06 | (2006.01) | |
| C12N 5/00 | (2006.01) | |
| C12N 15/00 | (2006.01) | |
| C07K 14/755 | (2006.01) | |
| C12N 9/64 | (2006.01) | |
| A61K 38/00 | (2006.01) | |

(52) U.S. Cl.
CPC .............. *C07K 14/755* (2013.01); *C12N 9/644* (2013.01); *C12Y 304/21022* (2013.01); *A61K 38/00* (2013.01)

(58) Field of Classification Search
None
See application file for complete search history.

(56) References Cited

U.S. PATENT DOCUMENTS

| | | | |
|---|---|---|---|
| 4,877,608 A | 10/1989 | Lee et al. | |
| 5,288,853 A | 2/1994 | Bhattacharva et al. | |
| 5,328,694 A | 7/1994 | Schwinn | |
| 5,565,427 A | 10/1996 | Freudenberg | |
| 5,605,884 A | 2/1997 | Lee et al. | |
| 5,733,873 A | 3/1998 | Osterberg et al. | |
| 5,831,026 A | 11/1998 | Almstedt et al. | |
| 5,874,408 A | 2/1999 | Nayar | |
| 6,005,077 A | 12/1999 | Schwarz et al. | |
| 6,887,852 B1 | 5/2005 | Paik et al. | |
| 7,247,707 B2 | 7/2007 | Besman et al. | |
| 8,329,871 B2 | 12/2012 | Borgvall et al. | |
| 2003/0077752 A1 | 4/2003 | Cho et al. | |
| 2005/0256038 A1 | 11/2005 | White et al. | |
| 2008/0207487 A1 | 8/2008 | DeFrees et al. | |
| 2011/0236412 A1 | 9/2011 | Drew | |

FOREIGN PATENT DOCUMENTS

| | | |
|---|---|---|
| AU | 687451 | 5/1995 |
| CA | 2065553 | 10/1992 |
| CN | 101260145 | 9/2008 |
| DE | 4001451 | 8/1991 |
| EP | 0157556 | 10/1985 |
| EP | 0508194 | 10/1992 |
| EP | 0774261 | 5/1997 |
| EP | 0774261 A2 | 5/1997 |
| EP | 1016673 | 7/2000 |
| EP | 1136553 | 9/2001 |
| EP | 1652534 | 5/2006 |
| EP | 1707634 | 10/2006 |
| EP | 1 739 179 | 1/2007 |
| EP | 1739179 A1 | 1/2007 |
| EP | 1739719 | 1/2007 |
| EP | 17391179 | 1/2007 |
| JP | 9221432 | 8/1997 |
| WO | EP-0157556 A2 * | 10/1985 |
| WO | 9118091 | 11/1991 |
| WO | 9407510 | 4/1994 |
| WO | 9408686 | 4/1994 |
| WO | 9426286 | 11/1994 |

(Continued)

OTHER PUBLICATIONS

Lind et al., Novel forms of B-domain-deleted recombinant factor VIII molecules construction and biochemical characterization, Eur J Biochemistry, 232: 19-27, 1995).*
Mei, Baisong, "Expression of Human Coagulation Factor VII . . . " Molecular Biotechnology, vol. 34, 2006, 165-178.
Picanco-Castro, V. "An enhancer/promoter combination strengthens the expression of blood-coagulation factor . . . " Genetics and Molecular Res. 7(2): 314-325 (2008)/.
Rodriguez et al. "Biosynthesis of FVIII in megakaryocytic cells: improved production and biochemical characterization." British Journal of Haematology, 127, 568-575, 2004.

(Continued)

*Primary Examiner* — Iqbal H Chowdhury
(74) *Attorney, Agent, or Firm* — Jacobson Holman PLLC

(57) ABSTRACT

A recombinant human factor VIII or IX protein having a human glycosylation pattern but the protein is devoid of N-glycolylneuraminic acid and/or the carbohydrate group Galα-3Gal.

18 Claims, 1 Drawing Sheet

(56) References Cited

FOREIGN PATENT DOCUMENTS

| WO | 9630041 | 10/1996 |
|---|---|---|
| WO | 9910011 | 3/1999 |
| WO | 0170968 | 9/2001 |
| WO | WO 01/70968 A2 | 9/2001 |
| WO | 03080108 | 10/2003 |
| WO | 2005121163 | 12/2005 |
| WO | 2007003582 | 1/2007 |
| WO | WO 2007/003582 A2 | 1/2007 |
| WO | 2007019331 | 2/2007 |
| WO | 2008008975 | 1/2008 |
| WO | 2008/073620 | 6/2008 |
| WO | 2008092643 | 8/2008 |
| WO | WO 2008/092643 A2 | 8/2008 |
| WO | 2009007451 | 1/2009 |
| WO | 2009/063069 | 5/2009 |
| WO | 2009077154 | 6/2009 |
| WO | 2009156430 | 12/2009 |
| WO | WO 2009/156430 A1 | 12/2009 |

OTHER PUBLICATIONS

Gil, Geun-Cheol et al. "Analysis of the N-glycans of recombinant of human Factor IX purified from transgenic pig milk." Glycobiology, vol. 18, No. 7, 526-539, 2008.

Andersson et al. "Isolation and characterization of human factor VIII: Molecular . . . " Proc. Natl. Acad. Sci. vol. 83, 2979-2973, May 1986.

Brinkhous et al. "Purified human factor VIII procoagulant protein: Comparative . . . " Proc. Natl. Acad. Sci. vol. 82, 8752-8756, Dec. 1985.

Chou "Inactivation of CMP-N-acetylneuraminic acid hydroxylase occurred prior to brain expansion during human evolution." Proc. Natl. Acad. vol. 99, No. 18, 11736-11741, 2002.

Courter et al. "Clinical Evaluation of B-Domain Deleted Recombinant Factor VIII in Previously Treated Patients." Seminars in Hematology, vol. 38, No. 2, suppl. 4, 44-51, 2001.

Ettingshausen et al. "Recombinant vs. plasma-derived products, especially those with intact VWF, regarding inhibitor development." Haemophilia, vol. suppl. 6, 102-106, 2006.

Galili et al. "Human natural anti-alpha-galactosyl IgG II. The specific recognition of alpha (1-3)-linked Galactose Residues." J. Exp. Med. vol. 162, 573-582, Aug. 1985.

Gensana et al. "Influence of von Willebrand factor on the reactivity of human factor VIII inhibitors with factor VIII." Haemophilia, vol. 7, 369-374, 2001.

Gitschier et al. "Characterization of the human factor VIII gene." Nature, vol. 312, 326-330, Nov. 22, 1984.

Hay. "The epdemiology of factor VIII inhibitors." Haemophilia, vol. 12, suppl. 6, 23-29, 2006.

Hironaka et al. "Structural Study of the Sugar Chains of Porcine Factor . . . " Archives of Biochemistry and Biophysics, vol. 307, No. 2, 316-330, Dec. 1993.

Hokke et al. "Structural analysis of the sialylated N- and O-linked carbohydrate chains . . . " Eur. J. Biochem. vol. 228, 981-1008, 1995.

Hokke et al. "Sialylated carbohydrate chains of recombinant human glycoproteins . . . " FEBS Letters, vol. 275, No. 1, 2, 9-14, Nov. 1990.

Kallas et al. "The von Willebrand factor collagen-binding activity asay: clinical application." Ann Hematol. vol. 80, 466-471, 2001.

Kawashima et al. "Characterization of Ganlioside Expression in Human Melanoma Cells: Immunological and Biochemical Analysis." J. Biochem. vol. 114, 186-193, 1993.

Lenting et al. "The Life Cycle of Coagulation Factor VIII in View of Its Structure and Function." Blood, vol. 92, No. 11, 3983-3996, Dec. 1, 1998.

Marquina et al. "Gangliosides Expressed in Human Breast Cancer." Cancer Research, vol. 56, 5165-5171, 1996.

Pittman et al. "Biochemical, Immunological and in Vivo Functional Characterization of B-Domain-Deleted Factor VII." Blood, vol. 81, No. 11, 2925-2935, Jun. 1, 1993.

Sandberg et al. Structural and Functional Characterization of B-Domain Deleted Recombinant Factor VII.: Seminars in Hematology, vol. 38, No. 2, suppl. 4, 4-12, Apr. 2001.

Tangvoranuntakul et al. "Human uptake and incorporation of an immunogenic nonhuman dietary sialic acid." Proc. Natl. Acad. Sci. vol. 100, No. 21, 12045-12050, Oct. 14, 2003.

Toole et al. "Molecular cloning of a cDNA encoding human antihaemophilic factor." Nature, vol. 312, 342-347, Nov. 22, 1984.

Vehar et al. "Structure of human factor VIII." Nature, vol. 312, 337-342, Nov. 22, 1984.

Wood et al. "Expression of active human factor VIII from recombinant DNA clones." Nature, vol. 312, 330-337, Nov. 22, 1984.

Bai et al. Renatruration and purification of rhGM-CSF with ion-exchange chromatography, Biotechnology Progress, vol. 23, No. 5, Sep. 2007, pp. 1138-1142.

Brochier et al. Fast purification process optimizing using mixed-mode chromatography sorbents in pre-packed mini-columns, Journal of Chromatography, vol. 1177, No. 2, Dec. 26, 2007, pp. 226-233.

Capto MMC/Data File 11-0035-45 AA, Internet Ciation, 2005, URL: http:www.gelifesciences.co.jp/catalog/pdr_attach/11003545AA.pdf.

GE healthcare Instructions for Capto MMC, Instructions 11-0035-05 AD, Mar. 2005, pp. 1-24, URL: http://www.gelifesicences.com/aptrix/upp00919.nsf/Content/D DE84FA9F53D2925C1257628001 D 1 EBF/$file/11003505AD.pdf.

Kaleas et al. Industrial case study: Evaluation of mixed-mode resin for selective capture of a human growth factor recombinantly expressed in *E. coli*, Journal of Chromatography, vol. 1217, No. 2, Jan. 8, 2010, pp. 235-242.

Pizarro et al. High-yield expression of human vascular endothelial growth factor VEGF165 in *Escherichia coli* and purification for therapeutic applications, Protein Expression and Purification, vol. 72, No.2, Mar. 17, 2010, pp. 184-193.

Rao et al., A purification method for improving the process yield and quality of recombinant human granulocyte colony-stimulating factor expressed in *Escherichia coli* and its characterization, Biotechnology and Applied BioChemistry, vol. 50, No. pt 2, Jun. 1, 2008.

Mei et al. Expression of human congulation Factor VIII in a human hybrid cell ine, HKB11, Molecular Biotechnology, vol. 34, 2006, pp. 165-178.

Andersson et al. Isolation and characterization of human factor VIII: Molecular forms in commercial factor VIII concentrate, cryoprecipitate, and plasma, Proc Natl Acad Sci, vol. 83, May 1986, pp. 2979-2983.

Brinkhous et al. Purified human factor VIII procoagulant protein: Comparative hemostatic responses after infusions into hemophilic and von Willebrand disease dogs, Proc Natl Acad Sci, vol. 82, Dec. 1985, pp. 8752-8756.

Chou et al. Inactivation of CMP-N-acetylneuraminic acid hydroxylase occurred prior to brain expansion during human evolution, Proc Natl Acad Sci, vol. 99, No. 18, Sep. 3, 2002, pp. 11736-11741.

Courter et al. Clinical evaluation of B-domain recombinant Factor VIII in previously treated proteins, Seminars in Hematology, vol. 38, No. 2, suppl 4, Apr. 2001, pp. 44-51.

Ettingshausen et al. Recombinant vs. plasma-derived products, especially those with intact VWF, regarding inhibitor development, Haemophilia, vol. 12, suppl 6, 2006, pp. 102-106.

Galili et al. Human natural anti-alpha-galactosyl IgG II. The specific recognition of alpha (1-3)-linked Galactose Residues, J. Exp. Med. vol. 162. Aug. 1985, pp.573-582.

Gensana et al. Influence of von Willebrand factor on the reactivity of human factor VIII Inhibitors with factor VIII, Haemophilia, vol. 7, 2001, pp. 369-374.

Gil et al. Analysis of the N-glycans recombinant human Factor IX purified from transgenic pig milk, Glycobiology, vol. 18, No. 7, 2008, pp. 526-539.

Gitschier et al. Characterization of the human factor VIII gene, Nature, vol. 312, Nov. 22, 1984, pp. 326-330.

Hay et al. The epdemiology of factor VIII inhibitors, Haemophilia, vol. 12, suppl. 6, 2006, pp. 23-29.

Hironaka et al. Structural study of the sugar chains of porcine factor VIII-Tissue- and species-specific glycosylation of Factor VIII, Archives of Biochemistry and Biophysics. vol. 307, No. 2, Dec. 1993, pp. 316-333.

(56) References Cited

OTHER PUBLICATIONS

Hokke et al. Sialylated carbohydrate chains of recombinant human glycoproteins expressed in Chinese hamster ovary cells contain traces of N-glycolyneuraminic acid, FEBS Letters, vol. 275, No. 1, 2, 9-14, Nov. 1990.

Hokke et al. Structural analysis of the sialylated N—and O—linked carbohydrate chains of recombinant huam erythropoietin expressed in Chinese hamster ovary cells, Eur. J. Biochem. vol. 228. 1995, pp. 981-1008.

Kallas et al. The von Willebrand factor collagen-binding activity assay: clinical application, Ann Hematol. vol. 80, 2001, pp. 466-471.

Kawashima et al. Characterization of Ganlioside expression in human melanoma cells: Immunological and biochemical analysis, J. Biochem, vol. 114, 1993, pp. 186-193.

Lenting et al. The life cycle of coagulation Factor VIII in view of its structure and function, Blood, vol. 92, No. 1, Dec. 1, 1998, pp. 3983-3996.

Lind et al. Novel forms of B-domain-deleted recombinant factor VIII molecules and biochemical characterization, Eur. J. Biochem, vol. 232, 1995, pp. 19-27.

Marquina et al. Gangliosides expressed in human breast cancer, Cancer Research, vol. 56, 1996, pp. 5165-5171.

Picano-Castro et al. An enhancer/promoter combination strengthens the expression of blood-coagulation factor VIII in non-viral expression vectors, Genetics and Molecular Res. 7(2), 2008, pp. 314-325.

Pittman et al. Biochemical; immunological, and in vivo functional characterization of B-domain-deleted Factor VIII, Blood, vol. 81, No. 11, Jun. 1, 1993, pp. 2925-2935.

Rodriguez et al. Biosynthesis of FVIII in megakaryocytic cells: Improved production and biochemical characterization, British Journal of Haematology, vol. 127, 2004, pp. 568-575.

Sandberg et al. Structural and functional characterization of B-domain deleted recombinant factor VIII, Seminars in Hematology, vol. 38, No. 2, suppl. 4, Apr. 2001, pp. 4-12.

Sandberg et al. Functional characteristics of the novel, human-derived recombinant FVIII protein product, human-dl rhFVIII, Thrombosis Research 130, 2012, pp. 808-817.

Tangvoranuntakul et al. Human uptake and incorporation of an immunogenic nonhuman dietary sialic acid, Proc Natl Acad Sci, vol. 100, No. 21, Oct. 14, 2003, pp. 12045-12050.

Toole et al. Molecular cloning of a cDNA encoding human antihaemophilic factor, Nature, vol. 312, Nov. 22, 1984, pp. 330-337.

Vehar et al. Structure of human factor VIII, Nature, vol. 312, Nov. 22, 1984, pp. 337-342.

Wood et al. Expression of active human factor VIII from recombinant DNA clones, Nature, vol. 312, Nov. 22, 1984, pp. 330-337.

Mollmann et al. The stability of insulin in solid formulations containing melezitose and starch. Effects of processing and excipients, Drug Development and Industrial Pharmacy, vol. 32. NR. 6, Jul. 2006, pp. 765-778.

Arakawa et al. Induced binding of proteins by ammonium sulfate in affinity and Ion-exchange column chromatography, J. Biochem, Biophys. Methods, vol. 70, 2007, pp. 493-498.

Bhattacharyya et al. Recombinant Factor VIII for haemophilia, An overview of production technologies, CRIPS, vol. 4, No. 3. Jul.-Sep. 2003, pp. 2-8.

Burton et al. Salt-independent adsorption chromatography: new broad-spectrum affinity method for protein capture, Biochemical and Biophysical Methods, vol. 49, 2001, pp. 275-287.

Eriksson et al. The manufacturing process for B-domain deleted recombinant Factor VIII, Seminars in Hematology, vol. 38, No. 2, suppl. 4, Apr. 2001, pp. 24-31.

Farrugia, Biotechnology and the plasma fractionation Industry—The impact of advances in the production of coagulation Factor VIII, Biotechnology, vol. 3, No. 1, Feb. 1993, pp. 16-20.

Johansson et al. Preparation and characterization of prototypes for multi-modal separation media aimed for capture of negatively charged biomolecules at high salt conditions, Journal of Chromatography, vol. 1016, 2003, pp. 21-33.

Johansson et al. Preparation and characterization of prototypes for multi-modal separation aimed for capture of positively charged biomolecules at high-salt conditions, Journal of Chromatography, vol. 1016, 2003, pp. 35-49.

Parti et al. In vitro stability of recombinant human factor VIII, Haemophilia, vol. 6, 2000, pp. 513-522.

Wang et al. Coagulation factor VIII: structure and stability, International Journal of Pharmaceutics, vol. 259, 2003, pp. 1-15.

Xindu et al. Liquid chromatography of recombinant proteins and protein drugs, Journal of Chromatography B, vol. 866, 2008, pp. 133-153.

Detergents Properties and Applications, Sigma Aldrich, p. 1 of 1, available online at http://www/sigmaaldrich.com/img/assets/15402/Detergent_Selection_Table.pdf.

Sandberg et al. Structural and functional characteristics of the B-domain deleted recombinant factor VIII protein, r-VIII SQ, Thromb Haemost, vol. 85, 2001, pp. 93-100.

* cited by examiner

RECOMBINANTLY PRODUCED HUMAN FACTOR VIII AND IX

This is a 371 of PCT/EP09/060,829 filed Aug. 21, 2009, claiming benefit of U.S. provisional application No. 61/136,250, filed Aug. 21, 2008, and claiming the priority of European number 08162765.5 filed Aug. 21, 2008, hereby incorporated by reference.

FIELD OF THE INVENTION

The present invention relates to a recombinantly produced human factor VIII and/or factor IX glycoprotein that has a human-like glycosylation pattern.

BACKGROUND OF THE INVENTION

Glycoproteins are abundant in the animal and plant kingdoms as well as in microorganisms. The carbohydrate moieties of glycoproteins have been shown to have multiple functions such as having important roles for cell to cell recognition, cell signalling, protein structure, protein protection, protein stabilisation, and protein to protein interaction. The carbohydrate chains of most glycoproteins are linked to proteins by either N-acetylglucosamine (GlcNAc) bound to the free amino groups of asparagine residues (N-linked carbohydrate) or by N-acetylgalactoseamine (GalNAc) bound to the hydroxyl groups of serine or threonine residues (O-linked carbohydrate). The carbohydrate moiety at each site is often composed of several monosaccharide units forming complex structures. Most glycoproteins contain several different carbohydrate chains in one molecule. The structures of asparagine-linked carbohydrates are of three types; high-mannose, complex and hybrid type. These all have a common pentasaccharide core, Man$\alpha$1-6(Man$\alpha$1-3)Man$\beta$1-4GlcNAc$\beta$1-4GlcNAc. In high-mannose type structures further mannose units are coupled to this core and in complex type structures, fucose, galactose, N-acetylglucoseamine and sialic acid are commonly found. Two or more antennae of monosaccharide units might extend from the common core. The hybride type of carbohydrate chains contains antennae of both the high mannose type and complex type.

Hemophilia is a group of hereditary genetic disorders that impair the body's ability to control blood clotting or coagulation. In its most common form, Hemophilia A, clotting factor VIII is deficient. In Hemophilia B, factor IX is deficient. Hemophilia A occurs in about 1 in 5,000-10,000 male births, while Hemophilia B occurs at about 1 in about 20,000-34,000. The Factor VIII protein is an essential cofactor in blood coagulation where factor IXa converts factor X to its activated form. The deficiency of factor VIII and factor IX, respectively, can be treated with plasma-derived concentrates of factor VIII and factor IX or with recombinantly produced factor VIII and factor IX. The treatment with factor VIII or factor IX concentrates has led to a normalized life of the hemophilia patients. However, a certain percentage of the Hemophilia A patients develop inhibitory antibodies directed against the infused factor VIII product resulting in an impaired therapeutic effect. In recent years the recombinant products produced in hamster cell lines have become more frequently used. However, some reports might suggest that these products cause a higher incidence of inhibitor formation than the plasma-derived ones (Ettingshausen and Kreuz, 2006; Hay, 2006).

The nascent form of factor VIII is a single chain of about 300 kDa consisting of domains described as A1-A2-B-A3-C1-C2 (Gitschier et al., 1984; Toole et al., 1984; Vehar et al., 1984; Wood et al., 1984). The protein undergoes processing prior to secretion into blood resulting in a heavy chain of about 200 kDa consisting of the A1-A2 domains and the major part of the B-domain and a light chain of 80 kDa consisting of the A3-C1-C2 domains (here called full-length factor VIII). The B-domain has been shown to be dispensible for the coagulant activity of factor VIII (Andersson et al., 1986; Brinkhous et al., 1985; Pittman et al., 1993). Therefore, it is possible to use factor VIII with a deleted B-domain in therapeutic use for the treatment of hemophilia A (Courter and Bedrosian, 2001).

In blood circulation the intact factor VIII is present in a tight complex with the high molecular mass protein, von Willebrand factor (vWF). vWF is not an enzyme and therefore has no catalytic activity. Its primary function is binding to other proteins, particularly factor VIII and it is important in platelet adhesion to wound sites. vWF is a large protein consisting of multiple monomers with a total molecular mass up to 20.000 kDa. As a carrier protein of factor VIII in the blood circulation vWF protects it from proteolytic degradation and thereby increases the in vivo survival of factor VIII. Furthermore, it has been suggested that the binding of vWF to factor VIII has a protective effect against recognition of factor VIII by the immune system and thereby resulting in a decreased risk for development of inhibiting antibodies against factor VIII (Gensana et al., 2001; Kailas and Talpsep, 2001).

The full-length factor VIII is a heavily glycosylated protein with 25 potential sites for N-linked glycosylation, of which the majority reside in the B-domain. Only six of these sites are localized within the A and C domains. Previously published data showed that four of the potential sites in the factor VIII A and C domains are glycosylated. These were Asn 41 and Asn 239 in the heavy chain and Asn 1810 and Asn 2118 in the light chain (Lenting et al., 1998; Sandberg et al., 2001). Thirteen sites for O-linked glycosylation were found in full-length recombinant factor VIII, most of them located in the B-domain (Lenting et al., 1998). The B-domain-deleted factor VIII, ReFacto®, was reported to have two sites substituted with O-linked carbohydrate chains (Sandberg et al., 2001).

Recombinant human proteins are most often expressed in murine cell lines. This means that although a human gene construct has been used for expression the proteins have murine glycosylation patterns. One such example is the antigenic carbohydrate group unbranched Gal$\alpha$1-3Gal, present in recombinant proteins produced from these cell lines (Galili et al., 1985; Hokke et al., 1995). However, this carbohydrate group is not present in native human glycoproteins. Another example is the composition of sialic acid types present. Recombinant proteins derived from murine cell lines have been reported in addition to the major form of sialic acid, N-acetylneuraminic acid (Neu5Ac), to also contain some percentage of the antigenic sialic acid, N-Glycolylneuraminic acid (Neu5Gc) (Hokke et al., 1990). Neu5Gc is normally absent in native human proteins due to a mutation in the gene coding the enzyme CMP-N-acetyl neuraminic acid hydroxylase, but present in all other mammalian glycoproteins (Chou et al., 2002). However, Neu5Gc has been reported to be present in rapidly growing cells such as human cancer cells and in human embryonic cells (Kawashima et al., 1993; Marquina et al., 1996; Tangvoranuntakul et al., 2003).

Most humans have been shown to have circulating antibodies both against the Gal$\alpha$1-3Gal epitope and the Neu5Gc.

Today, the recombinant human factor VIII products for therapeutic use are all derived from murine cell lines, which mean that they have a murine glycosylation pattern. Thus the antigenic carbohydrate group, unbranched Gal$\alpha$1-3Gal, might be present in factor VIII produced from these cell lines (Hironaka et al., 1993). However, this carbohydrate group is not present in the plasma-derived human factor VIII. Another example is the presence of the antigenic sialic acid N-glycolylneuraminic acid in factor VIII from murine cell lines.

Methods to produce recombinant factor VIII protein in human cell lines have been disclosed in the prior art. US-A-2006/099685 relates to a process for the production of a recombinant factor VIII protein in human embryonic retina cells focusing on the importance of said cells to express at least one adenoviral E1A protein. The recombinant protein produced according to this procedure is said to have a human glycosylation pattern different from the isolated human counterpart.

WO-A-2007/003582 provides a method for transfection and production of human recombinant proteins, in particular blood proteins, in human cell lines under serum- and protein-free conditions, stably transfected with a specific vector carrying the gene coding for the protein of interest.

US-A-2003/0077752 relates to glycosylated proteins having human factor VIII activity. The glycosylation pattern of this product contains alpha-(2,6)-linked sialic acid and bisecting N-acetylglucosamine linked to a core beta-mannose.

EP-A-0774261 discloses complexes of factor VIII and vWf and their therapeutic value.

B. Mei in Molecular Biotechnology Volume 34, 2006, 165-178; V. Picanco-Castro et al. in Genetics and Molecular Research 7 (2):314-325 (2008); M.-H. Rodriguez, British Journal of Haematology, 127, 568-575; G.-Ch. Gil, Glycobiology vol. 18 no. 7 pp. 526-539 as well as WO-A-2008/092643 disclose the production of recombinant factor IX or factor VIII in human cells.

It would be desirable with a recombinant human factor VIII product and recombinant human factor IX product with a human glycosylation pattern in order to minimise the immunogenicity of the recombinant protein when used in therapy.

SUMMARY OF THE INVENTION

The present invention relates to a recombinant human factor VIII or IX protein having a human-like glycosylation pattern. The protein is devoid of the sialic acid, N-glycolylneuraminic acid, and/or the carbohydrate group Galα-3Gal. The protein also shows a better binding to the von Willebrand factor than a corresponding recombinant protein produced in a non-mammalian cell line. The human glycosylation pattern might have a beneficial impact on the protein when used in therapy as it might improve the functional properties and/or decrease the immunogenicity.

The invention also relates to a recombinant human factor VIII protein having a human glycosylation pattern wherein the protein shows a better binding to the von Willebrand factor than a corresponding recombinant protein produced in a non-mammalian cell line.

Further embodiments will be apparent from the following description and the appended claims hereby incorporated in its entirety.

Figure 1:
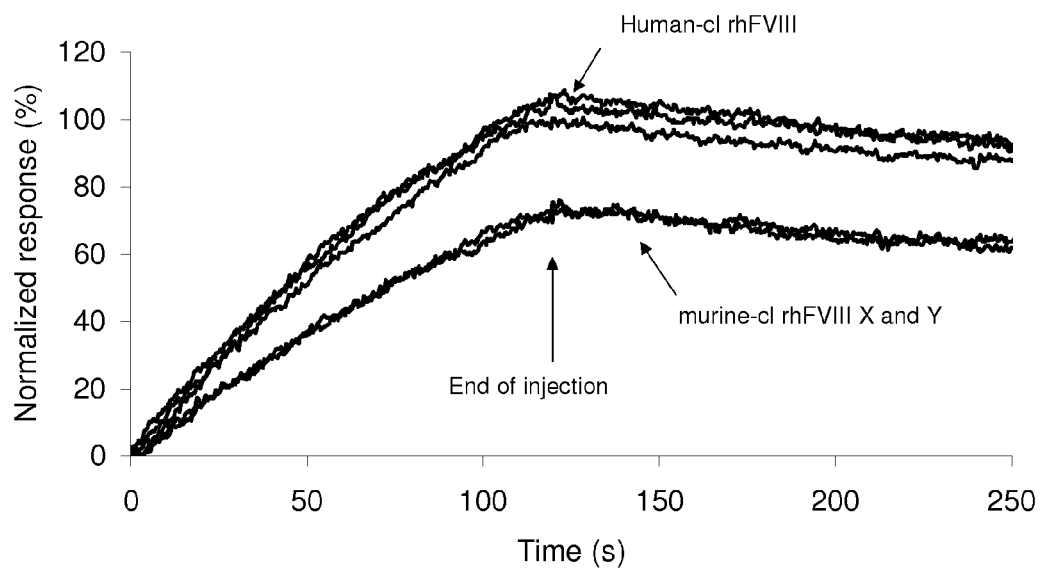
FIG. 1 is a diagram showing sensorgrams for the two minutes injection of 1 IU FVIII:C/mL of three batches of human-cl rhFVIII and murine-cl rhFVIII X and murine-cl rhFVIII Y across a vWF surface. All injections were performed in triplicates. For clarity only one injection for each FVIII molecule are shown. All responses were normalised to the response of the FVIII-molecule having the highest response at the end of injection.

It must be noted that, as used in this specification and the appended claims, the singular forms "a," "an," and "the" include plural referents unless the context clearly dictates otherwise.

Also, the term "about" is used to indicate a deviation of +/−2% of the given value, preferably +/−5%, and most preferably +/−10% of the numeric values, where applicable.

In the context of the present invention the term "devoid" means being without a particular feature or characteristics as well as being without a particular feature or characteristics not detectable with standard liquid chromatographic methods, such as, but not limited to, HPAEC-PAD (high-performance anion-exchange chromatography with pulsed amperometric detection).

In the context of the present invention the term "sialic acid" relates to any member of a family of nine-carbon carboxylated sugars. The most common member of the sialic acid family is N-acetyl-neuraminic acid (2-keto-5-acetamido-3,5-dideoxy-D-glycero-D-galactononulopyranos-1-onic acid (often abbreviated as Neu5Ac, NeuAc, or NANA). A second member of the family is N-glycolyl-neuraminic acid (Neu5Gc or NeuGc), in which the N-acetyl group of NeuAc is hydroxylated.

In the context of the present invention the term "affinity" relates to the phenomenon whereby certain atoms or molecules have the tendency to aggregate or bond. The equilibrium dissociation constant ($K_D$) is commonly used, for example, to describe the affinity between a ligand and a protein i.e. how tightly a ligand binds to a particular protein. The $K_D$ has molar units (M), which corresponds to the concentration of ligand at which the binding site on a particular protein is half occupied, i.e. the concentration of ligand, at which the concentration of protein with ligand bound, equals the concentration of protein with no ligand bound. The smaller the $K_D$, the more tightly bound the ligand is, or the higher the affinity between ligand and protein. For example, a ligand with a nanomolar (nM) $K_D$ binds more tightly to a particular protein than a ligand with a micromolar (μM) $K_D$.

In the context of the present invention the term "binding capacity" relates to the extent to which the recombinat human factor VIII can bind to the von Willebrand factor (vWF), i.e. it relates to the number of factor VIII molecules in a product with ability to bind to the vWF. Binding capacity can be estimated by methods well known to a person skilled in the art.

In the context of the present invention the term "immortalized human cell line" refers to human cells that are not primary cells taken directly from an organism. In particular it refers to permanently established cell culture that will proliferate indefinitely given appropriate fresh medium and space, and thus have escaped the Hayflick limit (i.e. the number of times a cell will divide before it stops due to the telomere reaching a critical length).

DETAILED DESCRIPTION OF THE INVENTION

The present invention provides a new recombinant human factor VIII and/or IX glycoprotein. The recombinantly produced factor VIII and/or IX protein of the present invention is produced in a human cell line meaning that the protein will have a human-like glycosylation pattern. Thus, the skilled person would expect that the human factor VIII and/or IX show a human glycosylation pattern.

However, it has surprisingly been found that the recombinantly produced factor VIII and/or factor IX protein of the present invention is devoid of the antigenic sialic acid N-glycolylneuraminic acid and/or the antigenic carbohydrate group Galα-3Gal. As human cancer cells or rapidly growing human foetal cells have been found to express N-glycolylneuraminic acid it was expected that the recombinantly produced factor VIII and/or IX protein would have the N-glycolylneuraminic acid since they were produced in a human immortalized foetal cell line. This feature and/or the lack of the antigenic carbohydrate group Galα-3Gal and the overall human glycosylation pattern of the recombinant factor VIII and/or factor IX protein will be expected to have a beneficial impact on the product as it decreases the immunogenicity and also improves the functional properties of the protein. One such property of recombinant factor VIII is a better binding to the von Willebrand factor (vWF).

In one embodiment the present invention relates to a recombinant factor VIII or IX protein having a human glycosylation pattern and being devoid of antigenic N-glycolylneuraminic acid and/or Galα1-3Gal.

In another embodiment the present invention relates to a recombinant factor VIII protein that is devoid of antigenic N-glycolylneuraminic acid and/or Galα1-3Gal showing a better binding to the vWF than that of recombinant factor VIII protein produced in non-human mammalian cells, for example but not limited to, murine cells, such as Chinese hamster ovary (CHO) cells and Baby hamster kidney (BHK) cells. Better binding relates to the affinity to human vWF that is higher than that of recombinant factor VIII produced in non-human mammalian cells. In one particular embodiment, the affinity to the vWF is at least about 10-60% higher, preferably about 20%, 30%, 40%, 50% or 60% higher than that of recombinant factor VIII produced in non-human mammalian cells.

Affinity can also be estimated by the equilibrium dissociation constant ($K_D$). Thus, in yet another embodiment of the present invention the affinity between the recombinant protein and the vWF has a lower $K_D$ than factor VIII produced in non-human mammalian cells, for example but not limited to, murine cells, such as Chinese hamster ovary (CHO) cells and Baby hamster kidney (BHK) cells.

Further, better binding to the vWF also relates to the binding capacity. Thus, the present invention also relates to the recombinantly produced factor VIII glycoprotein having a binding capacity to the vWF that is higher than that of recombinant factor VIII produced in non-human mammalian cells, for example but not limited to, murine cells, such as Chinese hamster ovary (CHO) cells and Baby hamster kidney (BHK) cells. In one particular embodiment, the binding capacity to the vWF is at least about 10-60% higher as tested in the same experiment, preferably about 20%, 30%, 40%, 50% or 60% higher than that of recombinant factor VIII produced in non-human mammalian cells.

The recombinant factor VIII protein according to the invention being devoid of the antigenic sialic acid N-glycolylneuraminic acid and/or the antigenic carbohydrate group Galα-3Gal is in one embodiment a deletion derivative of native factor VIII, partially, or entirely lacking the B-domain of native factor VIII. In one embodiment the deleted B-domain is replaced by a linker peptide, comprising 10 to 25, preferably 14 to 20 amino acid residues. For more details about the B-domain deletion derivative and the linker see WO-A-01/70968 and WO-A-2007/003582, which are hereby incorporated in their entirety.

Thus, the present invention relates to a recombinant factor VIII glycoprotein having a human-like glycosylation pattern and having a better binding to human vWF than that of recombinant factor VIII produced in non-human mammalian cells, for example, but not limited to, murine cells such as Chinese hamster ovary (CHO) cells and Baby hamster kidney (BHK) cells. Better binding to the vWF relates to the affinity to the vWF and the binding capacity as defined above.

In an embodiment the recombinant protein having a human-like glycosylation pattern and a better binding to human vWF than that of recombinant factor VIII produced in non-human mammalian cells is a deletion derivative of native factor VIII, partially, or entirely lacking the B-domain of native factor VIII. In one embodiment the deleted B-domain is replaced by a linker peptide, comprising 10 to 25, preferably 14 to 20 amino acid residues. For more details about the B-domain deletion derivative and the linker see WO-A-01/70968 and WO-A-2007/003582, which are hereby incorporated in their entirety.

The recombinant human factor VIII and/or IX glycoprotein as defined above is preferably produced in a human cell line, preferably an immortalized human cell line. Non-limiting examples of such cell lines are kidney, bladder, liver, lung, cardiac muscle, smooth muscle, ovary, retina, nerve and gastrointestinal cell lines.

In one particular embodiment the inventive protein is produced in an immortalized human embryonic kidney cell line (HEK). Non-limiting examples of such cell lines are HEK293 (ATCC CRL-1573; DSM ACC 305; ECACC ref: 85120602), HEK293T (ATCC CRL 11268; DSM ACC 2494) and HEK293F (Invitrogen R79007). In one particular embodiment the human cell line is HEK293F (Invitrogen R79007).

In yet another embodiment the present invention relates to a recombinant protein as defined above having lower immunogenicity compared to a human recombinant factor VIII or IX protein produced in a non-human cell line, for example but not limited to, murine cells such as Chinese hamster ovary (CHO) cells and Baby hamster kidney (BHK) cells.

The present invention also relates to a pharmaceutical composition comprising the inventive protein as defined above in admixture with a pharmaceutically acceptable excipient. The pharmaceutical composition comprises the recombinant factor VIII or IX protein in a therapeutically effective dose. Dosage and duration of treatment depend on the severity of the factor VIII and/or factor IX deficiency, the location and extent of bleeding, and the patient's clinical condition. Individual patients may vary in their response to factor VIII and factor IX, achieving different levels of in vivo recovery and demonstrating different half-lives. Doses administered should be titrated to the patient's clinical response by a practitioner skilled within the art. In the presence of an inhibitor, higher doses or appropriate specific treatment may be required. The number of units of factor VIII or factor IX administered is expressed in International Units (IU), which is related to the current WHO standard for factor VIII or IX products. Factor VIII activity in plasma is expressed either as a percentage (relative to normal human plasma) or in International Units (relative to an International Standard for factor VIII in plasma).

One international unit (IU) of factor VIII activity corresponds approximately to the quantity of factor VIII activity in one mL of normal human plasma. The calculation of the required dosage of factor VIII is based upon the empirical finding that 1 IU, of factor VIII per kg body weight raises the plasma factor VIII activity by approximately 2 IU/dL.

The dose to be administered and the frequency of application in treatment of haemophilia A is dependant on the clinical effectiveness in the individual patient. The usual prophylactic dose is 20-40 IU/kg body weight every 2-3 days.

In one embodiment the invention relates to a method for the treatment of a factor VIII- and/or a factor IX-associated disorder, such as hemophilia A and hemophilia B, wherein a recombinant protein as defined above is administered together with a pharmaceutically acceptable excipient in a therapeutically acceptable amount. Pharmaceutically acceptable excipients are well known to a person skilled in the art.

The present invention also relates to the use of a recombinant protein as defined above for the treatment of a factor VIII- and/or a factor IX-associated disorder, such as hemophilia A and hemophilia B. The recombinant protein according to the invention can be administered with standard methods in this field of therapy, such as, but not limited to, injections and infusions, subcutaneously or intravenously.

In another embodiment, the present invention relates to the use of a recombinant protein as defined above for manufacturing a medicament for the treatment of a factor VIII- and/or a factor IX-associated disorder, such as hemophilia A and hemophilia B. The medicament can be administered with standard methods in this field of therapy, such as, but not limited to, injections and infusions, subcutaneously or intravenously.

In yet another embodiment, the present invention relates to a complex between the protein as defined above and the von Willebrand factor wherein the protein is recombinant factor VIII. The complex has an improved binding affinity between the inventive protein and the vWF leading to a prolonged survival of the recombinant factor VIII in vivo.

The present invention will now be further described in the following non-limiting examples Example 1

A human B-domain-deleted factor VIII protein, human cell line recombinant human factor VIII (human-cl rhFVIII), was produced in the human cell line HEK293F according to the process described in EP-A-1 739 179 (Schröder et al., 2007b; Schröder et al., 2007a). The purification process consisted of five chromatography steps and generated a highly pure factor VIII protein (Winge et al., 2008).

The sialic acids of purified factor VIII protein (400-600 μg) of which 10 μg of Ketodeoxynonulosonic acid (KDN; internal standard) had been added were acid hydrolysed using 0.1 M Hydrochloric acid (80° C. for 1 hour). The products were purified using Dowex cation exchange chromatography and the resulting solution was lyophilized, resuspended in water and analysed by HPAEC-PAD. A standard mixture containing 5 μg each of Neu5Ac and NeuGc and 10 μg KDN and a reagent blank with 10 μg of KDN were hydrolysed and analysed in parallel with the samples.

Table 1 and 2 show the results from analysis of Neu5Ac and NeuGc of two samples A and B of human-cl rhFVIII. It is shown that the sialic acid type NeuGc is not detectable. Only Neu5Ac was found.

TABLE 1

Quantitation by HPAEC-PAD of N-Acetylneuraminic acid (Neu5Ac) and N-Glycolylneuraminic acid (NeuGc) released by acid from rhFVIII

| Sample | Neu5Ac nmoles/ml | NeuGc nmoles/ml |
|---|---|---|
| Standard mixture of 5 μg Neu5Ac and 5 μg NeuGc | 16 | 15 |
| human-cl rhFVIII, sample A, aliquot 1 | 9 | Not detected |
| human-cl rhFVIII, sample A, aliquot 2 | 11 | Not detected |
| human-cl rhFVIII sample A, aliquot 3 | 13 | Not detected |

TABLE 2

Quantitation by HPAEC-PAD of N-Acetylneuraminic acid (Neu5Ac) and N-Glycolylneuraminic acid (NeuGc) released by acid from rhFVIII

| Sample | Neu5Ac nmoles/ml | NeuGc nmoles/ml |
|---|---|---|
| Standard mixture of 5 μg Neu5Ac and 5 μg NeuGc | 16 | 15 |
| human-cl rhFVIII, sample B, aliquot 1 | 8 | Not detected |
| human-cl rhFVIII, sample B, aliquot 2 | 8 | Not detected |

Example 2

The binding of human-cl rhFVIII to human von Willebrand factor was analyzed using surface plasmon resonance with the Biacore 3000 instrument. The recombinant factor VIII products X and Y derived from murine cell lines (murine-cl rhFVIII X and Y) were used as comparators.

The von Willebrand factor was immobilized through primary amines to the carboxymethylated dextran of a CM5 sensor chip. The binding data were globally fit to a simple interaction model yielding kinetic parameters and affinities. The kinetics in binding and affinity to von Willebrand factor were analyzed. Furthermore, a quantitative measure of the capacity of Human-cl rhFVIII to bind to von Willebrand factor in comparison with other recombinant factor VIII products was obtained.

Table 3 below shows the kinetic parameters and affinities obtained for human-cl rhFVIII in comparison to murine-cl rhFVIII products X and Y. It is shown that human-cl rhFVIII has a significantly higher affinity, about 50-60%, to von Willebrand factor than the murine-cl rhFVIII products.

TABLE 3

Kinetic parameters and affinities of the interaction between human-cl rhFVIII and von Willebrand factor in comparison to murine-cl rhFVIII X and Y.

| Protein | Kinetic parameter $k_{on} \cdot 10^6$ (M$^{-1}$·s$^{-1}$) | $k_{off} \cdot 10^{-4}$ (s$^{-1}$) | Affinity $K_D$ (pM) |
|---|---|---|---|
| Human-cl rhFVIII (n = 27) | 4.5 ± 0.3 | 9.5 ± 1.2 | 210 |
| Murine-cl rhFVIII X (n = 6) | 3.3 ± 0.4 | 10.5 ± 0.2 | 320 |
| Murine-cl rhFVIII Y (n = 3) | 3.1 ± 0.2 | 10.5 ± 0.7 | 340 | n = Number of binding analyses

Figure 2:
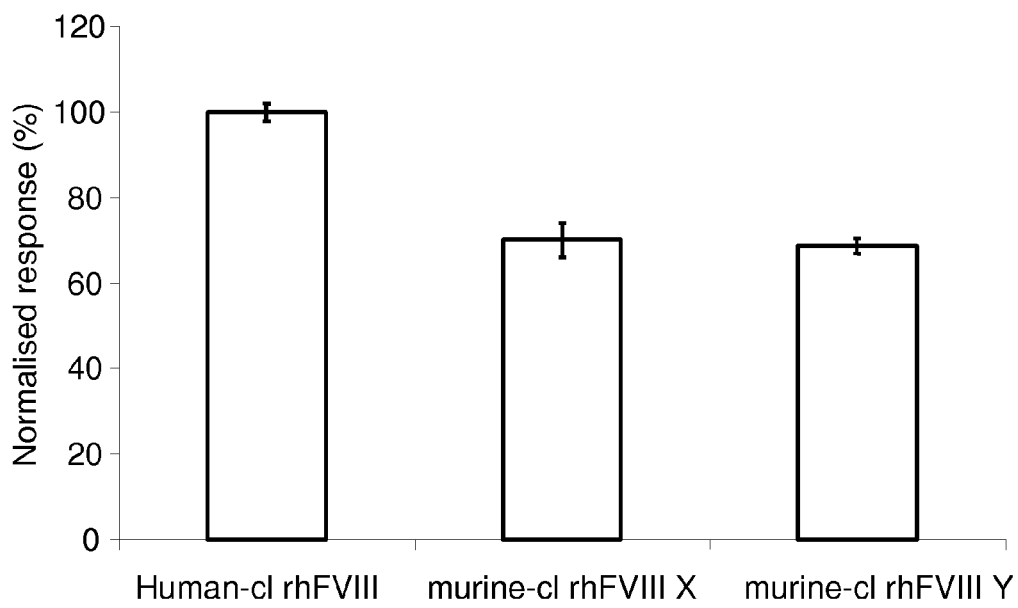
FIG. 2 is a diagram showing normalised responses with standard deviations 10 sec after the end of injection of 1 IU/mL of the different rhFVIII products. The human-cl rhFVIII bar represents the average responses for three human-cl rhFVIII batches. All responses were normalised to the response of the FVIII-molecule having the highest response 10 seconds after the end of injection Before the present invention is described, it is to be understood that the terminology employed herein is used for the purpose of describing particular embodiments only and is not intended to be limiting, since the scope of the present invention will be limited only by the appended claims and equivalents thereof.

FIGS. 1 and 2 show the results from quantitative measure of the capacity of human-cl rhFVIII to bind to von Willebrand factor in comparison to murine-cl rhFVIII products X and Y. Each FVIII product was injected for two minutes across the same surface with immobilized von Willebrand factor at a concentration of 1 international unit of factor VIII activity per mL. The result indicates that a significantly larger portion (about 40% more) of human-cl rhFVIII can bind to von Willebrand factor than is the case for the murine-cl rhFVIII products.

Although particular embodiments have been disclosed herein in detail, this has been done by way of example for purposes of illustration only, and is not intended to be limiting with respect to the scope of the appended claims that follow. In particular, it is contemplated by the inventor that various substitutions, alterations, and modifications may be made to the invention without departing from the spirit and scope of the invention as defined by the claims.

REFERENCE LIST

Andersson, L. O., Forsman, N., Huang, K., Larsen, K., Lundin, A., Pavlu, B., Sandberg, H., Sewerin, K., and Smart, J. (1986). Isolation and characterization of human factor VIII: molecular forms in commercial factor VIII concentrate, cryoprecipitate, and plasma. Proc. Natl. Acad. Sci. U.S.A 83, 2979-2983.

Brinkhous, K. M., Sandberg, H., Garris, J. B., Mattsson, C., Palm, M., Griggs, T., and Read, M. S. (1985). Purified human factor VIII procoagulant protein: comparative hemostatic response after infusions into hemophilic and von Willebrand disease dogs. Proc. Natl. Acad. Sci. U.S.A 82, 8752-8756.

Chou, H. H., Hayakawa, T., Diaz, S., Krings, M., Indriati, E., Leakey, M., Paabo, S., Satta, Y., Takahata, N., and Varki, A. (2002). Inactivation of CMP-N-acetylneuraminic acid hydroxylase occurred prior to brain expansion during human evolution. Proc. Natl. Acad. Sci. U.S.A 99, 11736-11741.

Courter, S. G. and Bedrosian, C. L. (2001). Clinical evaluation of B-domain deleted recombinant factor VIII in previously untreated patients. Semin. Hematol. 38, 52-59.

Ettingshausen, C. E. and Kreuz, W. (2006). Recombinant vs. plasma-derived products, especially those with intact VWF, regarding inhibitor development. Haemophilia. 12 Suppl 6, 102-106.

Galili, U., Macher, B. A., Buehler, J., and Shohet, S. B. (1985). Human natural anti-alpha-galactosyl IgG. II. The specific recognition of alpha (1- - - 3)-linked galactose residues. J. Exp. Med. 162, 573-582.

Gensana, M., Altisent, C., Aznar, J. A., Casana, P., Hernandez, F., Jorquera, J. I., Magallon, M., Massot, M., and Puig, L. (2001). Influence of von Willebrand factor on the reactivity of human factor VIII inhibitors with factor VIII. Haemophilia. 7, 369-374.

Gitschier, J., Wood, W. I., Goralka, T. M., Wion, K. L., Chen, E. Y., Eaton, D. H., Vehar, G. A., Capon, D. J., and Lawn, R. M. (1984). Characterization of the human factor VIII gene. Nature 312, 326-330.

Hay, C. R. (2006). The epidemiology of factor VIII inhibitors. Haemophilia. 12 Suppl 6, 23-28.

Hironaka, T., Furukawa, K., Esmon, P. C., Yokota, T., Brown, J. E., Sawada, S., Fournel, M. A., Kato, M., Minaga, T., and Kobata, A. (1993). Structural study of the sugar chains of porcine factor VIII-tissue- and species-specific glycosylation of factor VIII. Arch. Biochem. Biophys. 307, 316-330.

Hokke, C. H., Bergwerff, A. A., Van Dedem, G. W., Kamerling, J. P., and Vliegenthart, J. F. (1995). Structural analysis of the sialylated N- and O-linked carbohydrate chains of recombinant human erythropoietin expressed in Chinese hamster ovary cells. Sialylation patterns and branch location of dimeric N-acetyllactosamine units. Eur. J. Biochem. 228, 981-1008.

Hokke, C. H., Bergwerff, A. A., Van Dedem, G. W., van, O. J., Kamerling, J. P., and Vliegenthart, J. F. (1990). Sialylated carbohydrate chains of recombinant human glycoproteins expressed in Chinese hamster ovary cells contain traces of N-glycolylneuraminic acid. FEBS Lett. 275, 9-14.

Kallas, A. and Talpsep, T. (2001). von Willebrand factor in factor VIII concentrates protects against neutralization by factor VIII antibodies of haemophilia A patients. Haemophilia. 7, 375-380.

Kawashima, I., Ozawa, H., Kotani, M., Suzuki, M., Kawano, T., Gomibuchi, M., and Tai, T. (1993). Characterization of ganglioside expression in human melanoma cells: immunological and biochemical analysis. J. Biochem. 114, 186-193.

Lenting, P. J., van Mourik, J. A., and Mertens, K. (1998). The life cycle of coagulation factor VIII in view of its structure and function. Blood 92, 3983-3996.

Marquina, G., Waki, H., Fernandez, L. E., Kon, K., Carr, A., Valiente, O., Perez, R., and Ando, S. (1996). Gangliosides expressed in human breast cancer. Cancer Res. 56, 5165-5171.

Pittman, D. D., Alderman, E. M., Tomkinson, K. N., Wang, J. H., Giles, A. R., and Kaufman, R. J. (1993). Biochemical, immunological, and in vivo functional characterization of B-domain-deleted factor VIII. Blood 81, 2925-2935.

Sandberg, H., Almstedt, A., Brandt, J., Castro, V. M., Gray, E., Holmquist, L., Lewin, M., Oswaldsson, U., Mikaelsson, M., Jankowski, M. A., Bond, M., and Scoble, H. A. (2001). Structural and functional characterization of B-domain deleted recombinant factor VIII. Semin. Hematol. 38, 4-12.

Schröder, C., Wegmann, C., and Ding, H. Serum-free stable transfection and production of recombinant human proteins in human celllines. 05105965.7 [EP1739179A1]. 2007b. 2005b. Ref Type: Patent Schröder, C., Wegmann, C., and Ding, H. Serum-free stable transfection and production of recombinant human proteins in human celllines. PCT/EP2006/063705. 2007a. 2005a. Ref Type: Patent Tangvoranuntakul, P., Gagneux, P., Diaz, S., Bardor, M., Varki, N., Varki, A., and Muchmore, E. (2003). Human uptake and incorporation of an immunogenic nonhuman dietary sialic acid. Proc. Natl. Acad. Sci. U.S.A 100, 12045-12050.

Toole, J. J., Knopf, J. L., Wozney, J. M., Sultzman, L. A., Buecker, J. L., Pittman, D. D., Kaufman, R. J., Brown, E., Shoemaker, C., Orr, E. C., and (1984). Molecular cloning of a cDNA encoding human antihaemophilic factor. Nature 312, 342-347.

Vehar, G. A., Keyt, B., Eaton, D., Rodriguez, H., O'Brien, D. P., Rotblat, F., Oppermann, H., Keck, R., Wood, W. I., Harkins, R. N., and (1984). Structure of human factor VIII. Nature 312, 337-342.

Winge, S., Jernberg, M., Gilljam, G., Ericsson, U., and Borgvall, C. *A process of purifying coagulation factor VIII*. 08 158 893.1. 2008. Ref Type: Patent Wood, W. I., Capon, D. J., Simonsen, C. C., Eaton, D. L., Gitschier, J., Keyt, B., Seeburg, P. H., Smith, D. H., Hollingshead, P., Wion, K. L., and (1984). Expression of active human factor VIII from recombinant DNA clones. Nature 312, 330-337.

The invention claimed is:

1. A recombinant protein having a human-like glycosylation pattern but devoid of all N-glycolylneuraminic acid and carbohydrate group Galα-3Gal, wherein the recombinant protein is human factor VIII.

2. The recombinant protein of claim 1, wherein the factor VIII is a deletion modification of native factor VIII partially or entirely the B-domain of native factor VIII.

3. The recombinant protein according to claim 2 further comprising, in place of the partially or entirely lacking B-domain, a linker peptide having 10-25 amino acid residues.

4. The recombinant protein according claim 3 wherein the linker peptide has 14-20 amino acid residues.

5. The recombinant protein according to claim 1 having a higher affinity to von Willebrand factor than recombinant factor VIII produced in a non-human mammalian cell.

6. The recombinant protein of claim 5, wherein the mammalian cell is a murine cell.

7. The recombinant protein according to claim 1 having a higher binding capacity to von Willebrand factor than recombinant factor VIII produced in a non-human mammalian cell.

8. The recombinant protein of claim 7, wherein the mammalian cell is a murine cell.

9. The recombinant protein according to claim 2 having a higher affinity to von Willebrand factor than recombinant factor VIII produced in a non-human mammalian cell.

10. The recombinant protein according to claim 3 having a higher binding capacity to von Willebrand factor than recombinant factor VIII produced in a non-human mammalian cell.

11. The recombinant protein according to claim 1 produced in a human cell line.

12. The recombinant protein of claim 11, wherein the human cell line is an immortalized cell line selected from the group consisting of kidney, bladder, liver, lung, cardiac muscle, smooth muscle, ovary, retina, nerve, and gastrointestinal cell lines.

13. The recombinant protein according to claim 11, wherein the human cell line is a human embryonic kidney cell line (HEK).

14. The recombinant protein of claim 13, wherein the HEK is selected from the group consisting of HEK 293 (ATCC CRL-1573, DSM ACC 305, ECACC 85120602) and HEK 293F (Invitrogen R79007).

15. A pharmaceutical composition comprising the recombinant protein according to claim 1 and a pharmaceutically acceptable excipient.

16. A complex comprising the recombinant protein according to claim 1 and von Willebrand factor.

17. A pharmaceutical composition comprising the recombinant protein according to claim 2, and a pharmaceutically acceptable excipient.

18. A complex comprising the recombinant protein according to claim 2 and von Willebrand factor.

* * * * *

UNITED STATES PATENT AND TRADEMARK OFFICE
CERTIFICATE OF CORRECTION

PATENT NO. : 9,120,873 B2  Page 1 of 1
APPLICATION NO. : 12/737815
DATED : September 1, 2015
INVENTOR(S) : Helena Sandberg et al.

It is certified that error appears in the above-identified patent and that said Letters Patent is hereby corrected as shown below:

In the claims:

In claim 2, column 11, line 11, after "entirely" please add --lacking--.

Signed and Sealed this
Eighth Day of March, 2016

Michelle K. Lee
*Director of the United States Patent and Trademark Office*